United States Patent
Willner et al.

(10) Patent No.: US 7,485,212 B2
(45) Date of Patent: Feb. 3, 2009

(54) SELF-POWERED BIOSENSOR

(75) Inventors: Itamar Willner, Mevasseret Zion (IL); Evgeny Katz, Jerusalem (IL)

(73) Assignee: Yissum Reseach Development Company of the Hebrew University of Jerusalem, Jerusalem (IL)

( * ) Notice: Subject to any disclaimer, the term of this patent is extended or adjusted under 35 U.S.C. 154(b) by 779 days.

(21) Appl. No.: 10/487,694

(22) PCT Filed: Aug. 12, 2002

(86) PCT No.: PCT/IL02/00660

§ 371 (c)(1),
(2), (4) Date: Aug. 3, 2004

(87) PCT Pub. No.: WO03/019170

PCT Pub. Date: Mar. 6, 2003

(65) Prior Publication Data

US 2004/0245101 A1  Dec. 9, 2004

(30) Foreign Application Priority Data

Aug. 29, 2001 (IL) .................................. 145182

(51) Int. Cl.
*G01N 27/327* (2006.01)
(52) U.S. Cl. ................ 204/403.14; 204/409; 205/777.5
(58) Field of Classification Search ........................ None
See application file for complete search history.

(56) References Cited

U.S. PATENT DOCUMENTS

| 5,508,171 | A | | 4/1996 | Walling et al. |
| 5,593,852 | A | * | 1/1997 | Heller et al. ............... 435/14 |
| 5,639,672 | A | | 6/1997 | Burd et al. |
| 6,212,416 | B1 | | 4/2001 | Ward et al. |

FOREIGN PATENT DOCUMENTS

EP  0 300 082 A2  1/1989

(Continued)

OTHER PUBLICATIONS

I. Willner, E. Katz, F. Patolsky and A.F. Bückmann. J. Chem Soc. Perkin Trans. 2 (1998), p. 1817.*

(Continued)

*Primary Examiner*—Alex Noguerola
(74) *Attorney, Agent, or Firm*—The Nath Law Group; Susanne M. Hopkins; Ari G. Zytcer

(57) ABSTRACT

The present invention provides a system for the determination of an analyte in a liquid medium. The system comprises a self-powered biosensor and a detector for measuring an electrical signal generated by said biosensor while the analyte is being oxidized or reduced, the biosensor comprising a pair of electrodes, one of the electrodes being an anode and the other a cathode, both of which carry redox enzymes on their surface. An enzyme carried on one of the electrodes can catalyze an oxidation or reduction reaction in which the analyte is oxidized or reduced, respectively, and the other of said pair of electrodes carries on its surface enzymes that can catalyze a reaction in which the oxidizer or the reducer are reduced or oxidized, respectively, in the presence of the analyte.

23 Claims, 7 Drawing Sheets

FOREIGN PATENT DOCUMENTS

| | | |
|---|---|---|
| JP | 62 075346 | 4/1987 |
| WO | 97/19344 | 5/1997 |
| WO | 00/03447 A1 | 1/2000 |
| WO | 01/04626 A1 | 1/2001 |

OTHER PUBLICATIONS

Willner, I. et al., "Integration of Layered Redox Proteins and Conductive Supports for Bioelectronic Applications", *Angew. Chem. Int. Ed.*, vol. 39, No. 7, pp. 1180-1218, (2000).

Schuhmann, W. et al., "Electron Transfer between Glucose Oxidase and Electrodes via Redox Mediators Bound with Flexible Chains to the Enzyme Surface", *J. Am. Chem. Soc.*, vol. 113, No. 4, pp. 1394-1397, (1991).

Willner, I. et al., "Development of Novel Biosensor Enzyme Electrodes: Glucose Oxidase Multilayer Arrays Immobilized onto Self-Assembled Monolayers on Electrodes", *Adv. Mater.*, vol. 5, No. 12, pp. 912-915 (1993).

Heller, A., "Electrical Connection of Enzyme Redox Centers to Electrodes", *J. Phys. Chem.*, vol. 96, No. 9, pp. 3579-3587, (1992).

Willner, I. et al., "Electrical communication of redox proteins by means of electron relay-tethered polymers in photochemical, electrochemical and photoelectrochemical systems", *React. Polym.*, vol. 22, pp. 267-279, (1994).

Katz, E. et al., "A non-compartmentalized glucose | $O_2$ biofuel cell by bioengineered electrode surfaces", *J. Electroanalytical Chem. Soc.*, vol. 479, pp. 64-68, (1999).

Bardea, A. et al., "$NAD+$ -Dependent Enzyme Electrodes: Electrical Contact of Cofactor-Dependent Enzymes and Electrodes", *J. Am. Chem. Soc.*, vol. 119, No. 39, pp. 9114-9119, (1997).

Katz, E. et al., "Fully integrated biocatalytic electrodes based on bioaffinity interactions", *Biosens. Bioelectron.*, vol. 13, pp. 741-756, (1998).

Katz, E., et al., "A non-compartmentalized glucose/$O_2$ biofuel cell by bioengineered electrode surfaces", *Journal of Electroanalytical Chemistry*, vol. 479, pp. 64-68, (1999).

\* cited by examiner

SELF-POWERED BIOSENSOR

This application is a 371 of PCT/IL02/00660, filed on Aug. 12, 2002, which claims priority from Israeli application no. 145182, filed on Aug. 29, 2001.

FIELD OF THE INVENTION

This invention is in the field of bioelectronics and it relates generally to biosensors useful for measuring the concentration and/or the presence of organic analytes in liquid medium, e.g. medium of environmental, industrial, or clinical origin.

PRIOR ART

In the following description reference will be made to several prior art documents shown in the list of references below. The reference will be made by indicating in brackets their number from the list.
1. Willner I. and Katz E., Angew. Chem. Int. Ed., 2000, 39, 1180-1218.
2. (a) Schuhmann, W.; Ohara, T. J.; Schmidt, H. L.; Heller, A. J. Am. Chem. Soc., 1991, 113, 1394-1397. (b) Willner, I.; Riklin, A.; Shoham, B.; Rivenzon, D.; Katz, E. Adv. Mater., 1993, 5, 912-915.
3. (a) Heller, A. J. Phys. Chem. 1992, 96, 3579-3587. (b) Willner, I.; Willner, B. React. Polym. 1994, 22, 267-279.
4. Katz E., Willner I., Kotlyar A. B., J. Electroanalytical Chem. 1999, 479, 64-68.
5. (a) Bardea, A.; Katz, E.; B□ckman, A. F.; Willner, I. J. Amer. Chem. Soc. 1997, 119, 9114-9119. (b) Katz, E.; Heleg-Shabtai, V.; Bardea, A.; Willner, I.; Rau H. K.; Hechnel, W., Biosens. Bioelectron. 1998, 13, 741-756.

BACKGROUND OF THE INVENTION

A basic feature of a bioelectronic device is the immobilization of a biomaterial onto a conductive or semi-conductive support, and the electronic transduction of the biological functions associated with the biological substrates.

A biosensor is an analytical device incorporating biological and chemical sensing elements, either intimately connected to or integrated with a suitable transducer, which enables the conversion of concentrations of specific chemicals into electronic signals. A majority of biosensors produced thus far have incorporated enzymes as biological sensing elements (1). The electronic transduction of the enzyme-substrate interactions may also provide an analytical means to detect a respective substrate. The chemical means to assembly the enzymes on conductive or semi-conductive supports include the immobilization thereof on a substrate by means of self-assembling monolayers or thin films, polymer layers, membranes, carbon paste or sol-gel materials.

A specific class of enzymes which have been proposed for the use in analytical biochemical methods are redox enzymes. A redox reaction involves the transfer of electrons from the enzyme to the analyte—in a reduction reaction, or from the analyte to the enzyme in an oxidation reaction. If there is an electrical communication between the redox center of the enzyme molecules and the electrode material, there is an electrical charge flow which can serve as an indication of the presence of the analyte and the extent of charge flow may serve to measure the analyte's concentration. Alternatively, the determination may be based on the measurement of a product of the reaction by non-electrochemical means, e.g. by HPLC.

The direct electron transfer between the enzyme redox center and the electrode is limited, since the redox center is sterically insulated by the protein matrices. Consequently, the electrical communication between the redox enzymes and the electrodes may be established by an electron mediator group, often also termed "electron relay" (2), or by immobilizing the redox-proteins in electroactive polymers (3).

One of the attractive applications of bioelectrocatalytic electrodes is the development of biofuel cell assemblies. The biofuel cell utilizes biocatalysts for the conversion of chemical energy into electrical energy. Many organic substrates undergo combustion in oxygen or are oxidized with the release of energy. Methanol and glucose are abundant raw materials that can be used as biofuels which undergo oxidation, and molecular oxygen or hydrogen peroxide can act as the oxidizer.

For example, in a classical fuel cell where methanol is used as the fuel, the electro-oxidation of methanol at the anode can be represented by:

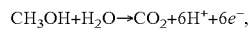

and the electro-reduction of oxygen at the cathode can be represented by:

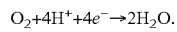

Protons generated at the anode are transported to the cathode. A flow of current is sustained by a flow of ions through the membrane separating the cell into cathodic and anodic compartments and a flow of electrons through the external load.

An example of a biofuel cell assembly based on the bioelectrocatalytic oxidation of glucose by $O_2$ (4) is showed schematically in FIG. 1. The cell consists of two electrodes, where the anode is functionalized by a surface-reconstituted glucose oxidase (GOx) monolayer and the cathode is modified with an integrated biocatalytic construction composed of cytochrome c (Cyt c) and cytochrome oxidase (COx). At the GOx monolayer-functionalyzed electrode, bioelectrocatalyzed oxidation of glucose to gluconic acid occurs, whereas at the Cyt c/COx layered electrode the reduction of $O_2$ to water takes place. The GOx layer is generated by the reconstitution of apo-GOx (GOx without its FAD cofactor) on amino-FAD covalently linked to a pyrroloquinolino quinone (PQQ) monolayer. The PQQ unit acts as an electron transfer mediator that bridges between the anode and the enzyme redox center.

A different approach to assemble biofuel cells is based on the bioelectrocatalyzed oxidation of 1,4-dihydronicotineamide cofactors. Various substrates, for example alcohols, hydroxy acids or sugars undergo biocatalyzed oxidation by enzymes dependent on the $NAD(P)^+$ cofactor (5).

The electrochemical, particularly amperometric biosensors, known in the art are powered by an external power source. This power source is used to apply external voltage to the electrodes and, thus, to polarize the electrodes and to provide electron transfer reactions.

The prior art teaches the use of amperometric biosensing systems as tools to accurately measure biological analytes of interest. However, many problems arise in the application of these biosensors, such as the relative sensitivity, selectivity and stability of the sensing device. In particular, some systems are prone to inaccuracies due to the presence of interfering agents present in the test samples. For example, the biocatalyzed oxidation of glucose is interfered by ascorbic acid or uric acid as contaminants of the analyte.

Thus, there is still a need in the art for biosensors which are highly selective, sensitive, and not prone to interference by other chemicals present in the sample.

SUMMARY OF THE INVENTION

It is an object of the present invention to provide an enzyme-based biosensor for determining the concentration and/or the presence of an organic substrate in a liquid.

It is a further object of the present invention to provide a method for measuring the concentration and/or the presence of an organic substrate in a liquid medium, that is applicable also for invasive measurement of analytes within body fluids in a tested subject.

It has been found in the present invention that a biofuel cell assembly consisting of two enzyme-electrodes connected by wires to a detector may be used as an analytical biosensor since the voltage and the current generated in the assembly are indicative of the quantity and/or the identity of the tested analyte. There is thus provided in the present invention, a biosensor that is self-powered by fluids that contain at least one substance capable to undergo biocatalyzed oxidation or reduction. The biosensor of the invention may be used in vivo as an implanted invasive device or ex vivo as a non-invasive device in the determination of the concentration and/or the identity of analytes in fluids of environmental, industrial, or clinical origin, e.g. blood tests, biocatalytic reactors, wine fermentation processes, etc. Furthermore, since no potential is applied to the electrodes, the operation of the biosensor is specific and is not interfered by contaminants.

In particular, the invention provides according to a first aspect, a system for the determination of an analyte in a liquid medium comprising a self-powered biosensor and a detector for measuring an electrical signal (voltage or current) generated by said biosensor while the analyte is being oxidized or reduced. The analyte is capable of undergoing a biocatalytic oxidation or reduction in the presence of an oxidizer or reducer, respectively. The biosensor comprises a pair of electrodes, one of the electrodes being an anode and the other a cathode, both of which carry redox enzymes on their surface, an enzyme carried on one of the electrodes can catalyze an oxidation or reduction reaction in which the analyte is oxidized or reduced, respectively, and the other of said pair of electrodes carrying on its surface enzymes that can catalyze a reaction in which the oxidizer or the reducer are reduced or oxidized, respectively; in the presence of the analyte.

The term "determination" should be understood as meaning the measurement of the concentration and/or the presence of a substance.

The enzymes carried by the electrodes are of redox type. The redox enzymes are dependent on co-factors such as for example: flavin adenine dinucleotide phosphate (FAD), pyrroloquinoline quinone (PQQ), nicotinamide adenine dinucleotide ($NAD^+$), nicotinamide adenine dinucleotide phosphate ($NADP^+$), hemes, iron-sulfur clusters and others.

The analytes that may be detected by the sensor of the invention are those capable to undergo biocatalytic oxidation or reduction reactions. Preferably, the analyte is usually an organic substance and the invention will be described hereinbelow with reference to oxidizable organic analytes. Examples of such analytes are sugar molecules, e.g. glucose, fructose, mannose, etc; hydroxy or carboxy compounds, e.g. lactate, ethanol, methanol, formic acid; amino acids or any other organic materials that serve as substrates for redox-enzymes.

Electrodes suitable for use in the biosensor of the present invention are made of conducting or semi-conducting materials, for example gold, platinum, palladium, silver, carbon, copper, indium tin oxide (ITO), etc. For invasive analyses the electrodes must be constructed of bio-compatible non hazardous substances, and fabricated as thin needles to exclude pain upon invasive penetration.

The biosensor of the invention is usually used without a membrane between the electrodes and this is a major benefit of the biosensor, especially when used in invasive applications. Nevertheless, the biosensor may also operate, when necessary, with a membrane.

The approaches used to modify the electrodes for use as biosensors can be divided into two groups: (a) modification of the electrode surface by deposition of a monolayer, which is based upon either the adsorption of a species at the electrode surface or a covalent attachment of a species, for example of electron mediator and enzyme, to the electrode, and (b) modification by a multilayer, which is most frequently achieved by the use of polymeric modifications of the electrode.

The anode, i.e. the working electrode, carries on its surface a layer comprising enzymes capable of catalyzing an oxidation reaction and preferably also an electron mediator group which can enhance the transfer of electrons between the anode and the enzyme.

The enzyme is preferably chosen according to its ability to oxidize a specific analyte. Therefore, the biosensor of the invention may also be used to establish the presence of a particular analyte. Enzymes which can be used in an anode configuration include glucose oxidase (GOx), in which case the analyte will be glucose, lactate dehydrogenase (LDH) for the conversion of lactate into pyruvate, fructose dehydrogenase, cholin oxidase, alcohol dehydrogenase, amino acid oxidase, etc.

Due to the inaccessible nature of the redox centers of redox enzymes, electron communication mediators are preferably added to biosensors either by physically admixing the mediator with the enzyme or by chemically binding the mediator to the enzyme to enhance electron transfer from a reactant or desired analyte through the enzyme to the electrode. For example, mediators for glucose sensors are electron acceptors, such as ferrocene derivatives, quinones, various organic dyes, organic redox polymers, e.g. polyaniline, inorganic redox matrices, e.g Prussian Blue, etc.

The cathode carries on its surface a layer comprising enzymes or enzyme-assemblies capable of catalyzing the reduction of an oxidizer, preferably oxygen, to water, and optionally a mediator that enhances the electrical contact between the cathode and the enzyme. Examples of such enzymes or enzyme assemblies are Laccase and a complex formed of Cytochrome c/Cytochrome oxidase (COx). In the case of Laccase, for example, electrons are finally transferred to the oxidizer, e.g. molecular oxygen ($O_2$), yielding water. The enzyme stores four electrons, and does not release intermediates in the $O_2$ reduction pathway. In the case of Cytochrome c/Cytochrome oxydase (COx), the Cytochrome c-mediated electron transfer to Cytochrome oxidase results also in the four-electron reduction of oxygen to water.

According to a second aspect, the present invention provides a method for determining an analyte in a liquid medium, said analyte being capable to undergo a biocatalytic oxidation or reduction reaction in the presence of an oxidizer or a reducer, respectively, the method comprising:

(i) providing the system of the invention;

(ii) contacting the biosensor of the system with the liquid medium;

(iii) measuring the electric signal generated between the cathode and the anode, the electric signal being indicative of the presence and/or the concentration of the analyte;

(iv) determining the analyte based on the electric signal.

When the liquid medium is, for example, a body fluid e.g. blood, lymph fluid or cerebro-spinal fluid, and the method is carried out in an invasive manner, the method comprises inserting the biosensor into the body and bringing it into contact with the body fluid and determining the analyte in the body fluid within the body. Alternatively, body fluids or any other analytes may be tested non-invasively, and in such cases the method comprises adding an oxidizer or a reducer to the medium.

Examples of analytes are sugar molecules e.g. glucose, fructose, maltose; lactate; billirubin; alcohols or amino acids.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF THE INVENTION

The following specific embodiments are intended to illustrate the invention and shall not be construed as limiting its scope.

Figure 1:
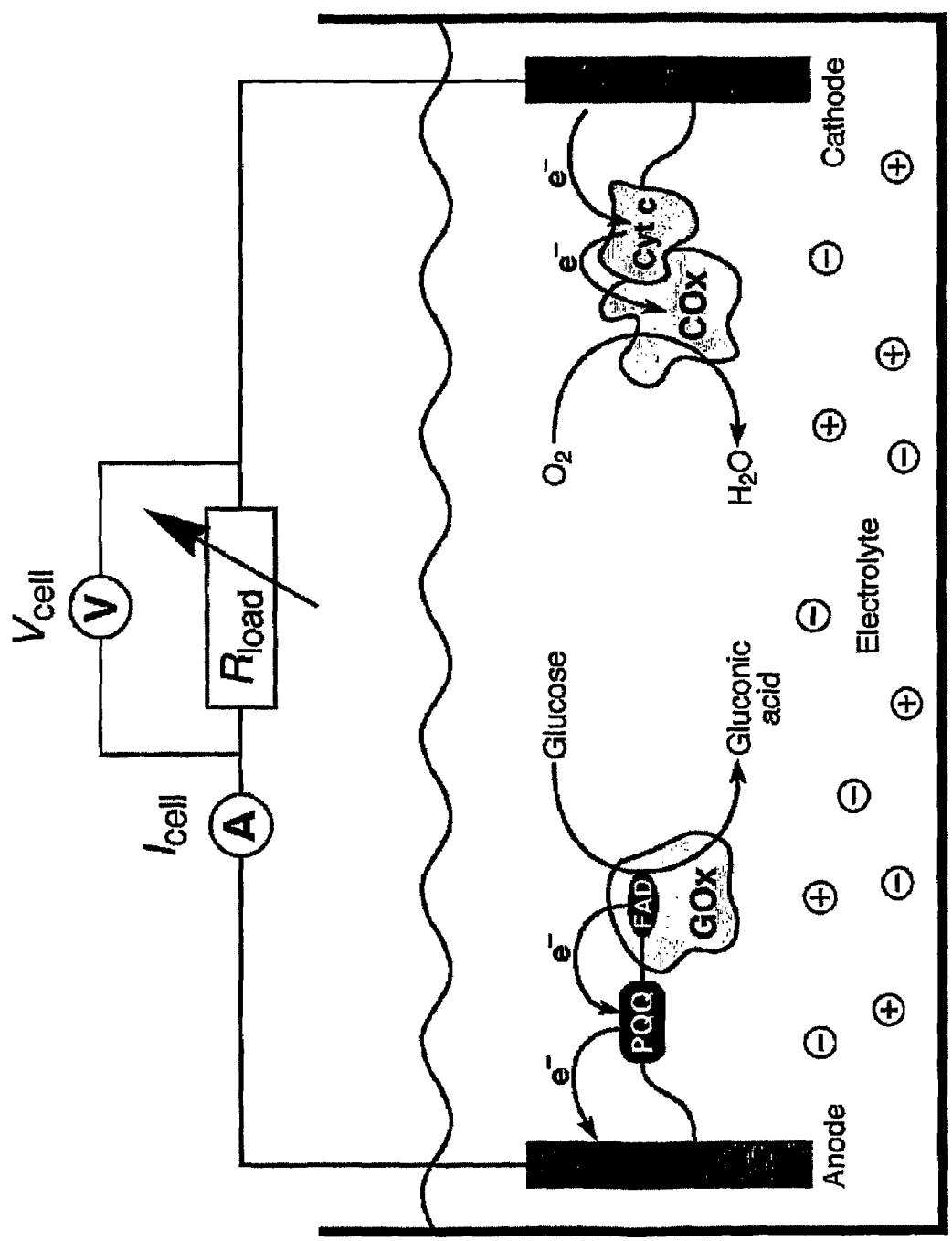
FIG. 1 is a schematic representation of a biofuel cell assembly based on the bioelectrocatalytic oxidation of glucose by $O_2$.
Figure 2A:
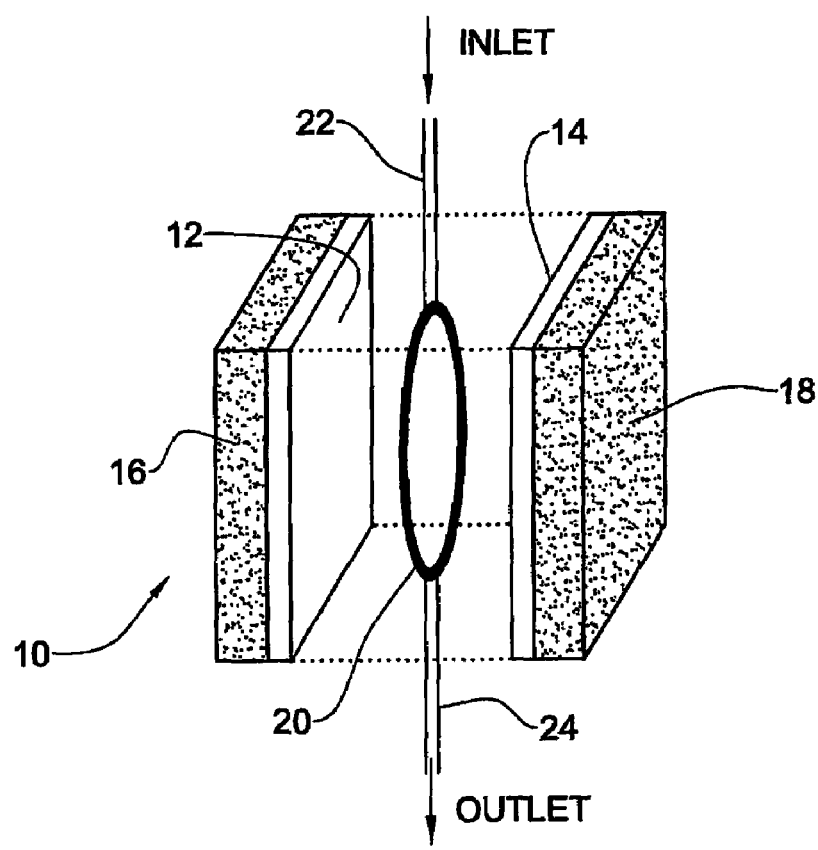
FIGS. 2A, 2B illustrate schematically a biosensor device according to the invention.
Figure 2B:
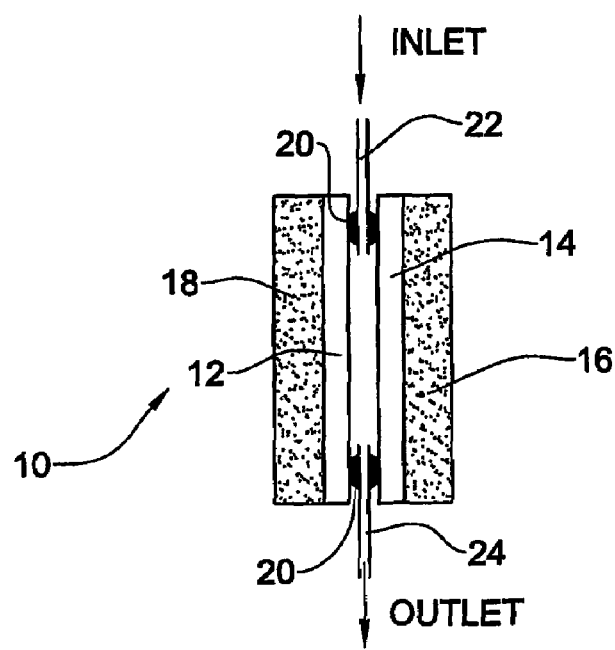

Reference is being made to FIGS. 2A and 2B that schematically show a simple configuration of a biosensor that may be used in the system of the invention. However, many other assemblies may be fabricated, that are based on the concept of the present invention. Thus, FIG. 2A shows a biosensor 10 (before assembling together all its parts) organized as a flow-injection cell that consists of two enzyme-functionalized Au-electrodes (ca. 0.19 cm active area), acting as anode 12 and cathode 14. Both electrodes are supported on glass plates 16 and 18 and are separated by a rubber O-ring 20 (ca. 2 mm thickness). Needles 22 and 24 implanted into the rubber ring convert the unit into a flow cell, where a liquid medium may flow at a flow rate of 1 mL min$^{-1}$. The distance between the cathode and the anode is ca. 2 mm. FIG. 2B shows the same device in assembled form.

It should be noted that the device shown in FIGS. 2A and 2B operates without a membrane and this is a significant advantage of the biosensor of the present invention, especially for invasive applications, since this possibility renders the biosensor configuration much simpler. However, although the biosensor of the invention preferably operates without a membrane between the electrodes, it may, at times, in non-invasive applications for example, also operate with a membrane.

The liquid medium comprises a solution having dissolved therein the analyte to be tested and an oxidizer. For example, in non-invasive applications, when the oxidizer is oxygen, the solution is saturated with oxygen prior to the analysis. During the operation of the biosensor, the concentration of the oxidizer should be kept constant. On the contrary, when it is desired to measure the concentration of oxygen instead of that of the analyte, then the concentration of the analyte should be kept constant.

Figure 3:
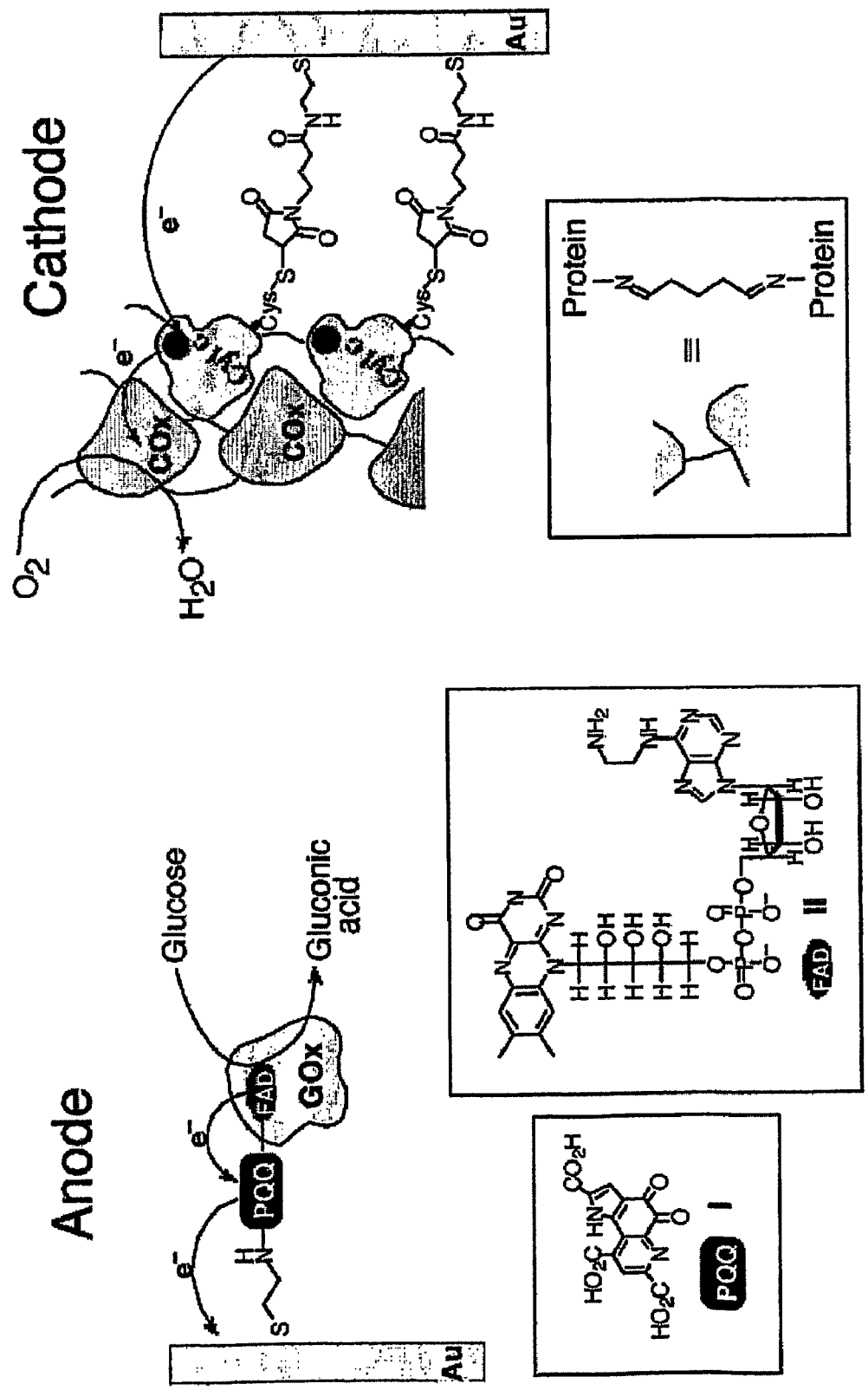
FIG. 3 is a schematic representation of the anode and cathode configurations for a glucose biosensor based on the enzyme GOx at the anode and Cyt c/COx at the cathode.

FIG. 3, shows the configuration of an anode and a cathode for a biosensor which measures the concentration of glucose. A glucose oxidase anode is generated by the reconstitution of apo-GOx on an aminoethyl flavineadenine dinucleotide phosphate (amino-FAD, compound II in FIG. 3), covalently linked to a pyrroloquinolino quinone (PQQ, compound I in FIG. 3) monolayer (1). The cathode consists of a glutaric dialdehyde-crosslinked Cyt c/COx monolayer assembled on an Au electrode.

Figure 4:
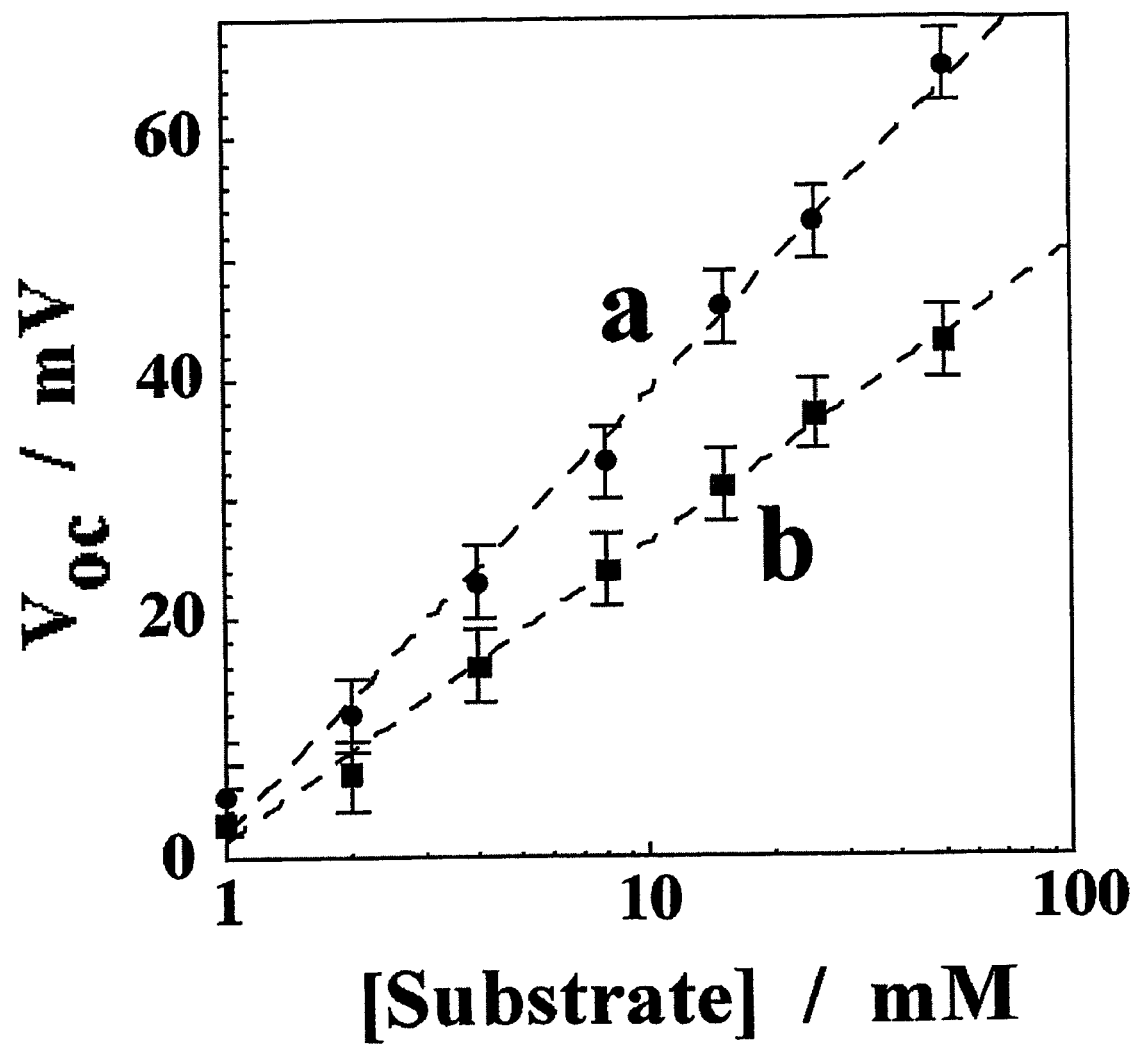
FIG. 4 is a graph showing two calibration curves: a) calibration curve for glucose; b) calibration curve for lactate.
Figure 5:
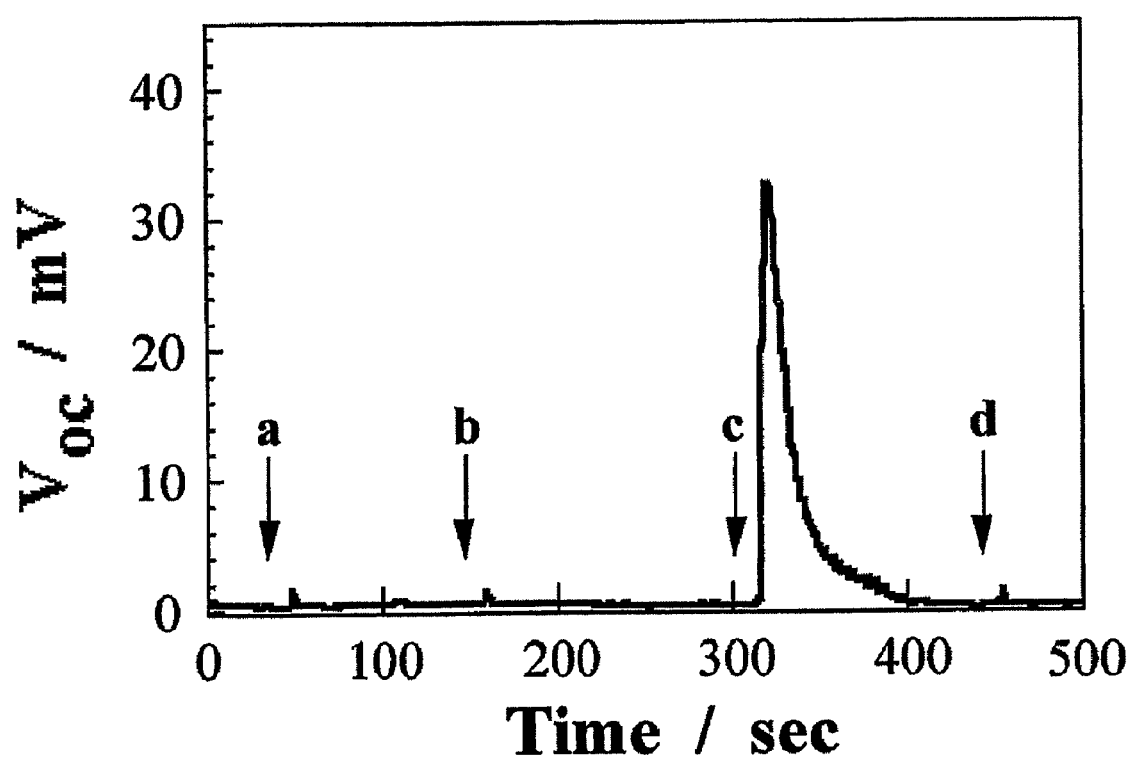
FIG. 5 is a graph showing the open-circuit voltage ($V_{oc}$) of a biofuel cell-based biosensor composed of the PQQ-FAD/GOx and Cyt c/COx-functionalized electrodes upon injections of: (a) 0.1 M phosphate buffer saturated with air (b) 50 mM ascorbic acid saturated with air, (c) 8 mM glucose saturated with air, (d) 50 mM glucose without $O_2$ (under Ar atmosphere). The arrows show the injection time. Phosphate buffer, 0.1 M, pH=7.0, equilibrated with air was used as a background electrolyte unless otherwise stated; temperature, ca. 30° C.

FIG. 4 shows the open circuit voltage ($V_{OC}$) of the glucose powered cell showed in FIG. 3, upon the injection of variable glucose concentrations into the two-electrode cell under flow conditions. The calibration curve follows a logarithmic relation as expected for a Nernstian-controlled concentration-dependence of the electrode potential. Glucose is sensed in concentration range of 1 mM-80 mM. There is no voltage output in the absence of glucose (FIG. 5, injection (a)). The self-powered cell is stable for 5 h at 30° C. under continuous operating conditions. The anode and cathode are stable for at least 2 months upon storage in the dry state at 0° C. The voltage cell is not perturbed upon addition of ascorbic acid, 50 mM (FIG. 5, injection (b)). Also, no voltage is developed in the cell upon the addition of glucose 50 mM, under an inert atmosphere of argon (FIG. 5, injection (d)). This later experiment clearly indicates that the sensing of glucose by the cell requires the simultaneous oxidation (of glucose) and reduction (of oxygen to water) by the anode and cathode, respectively.

Figure 6:
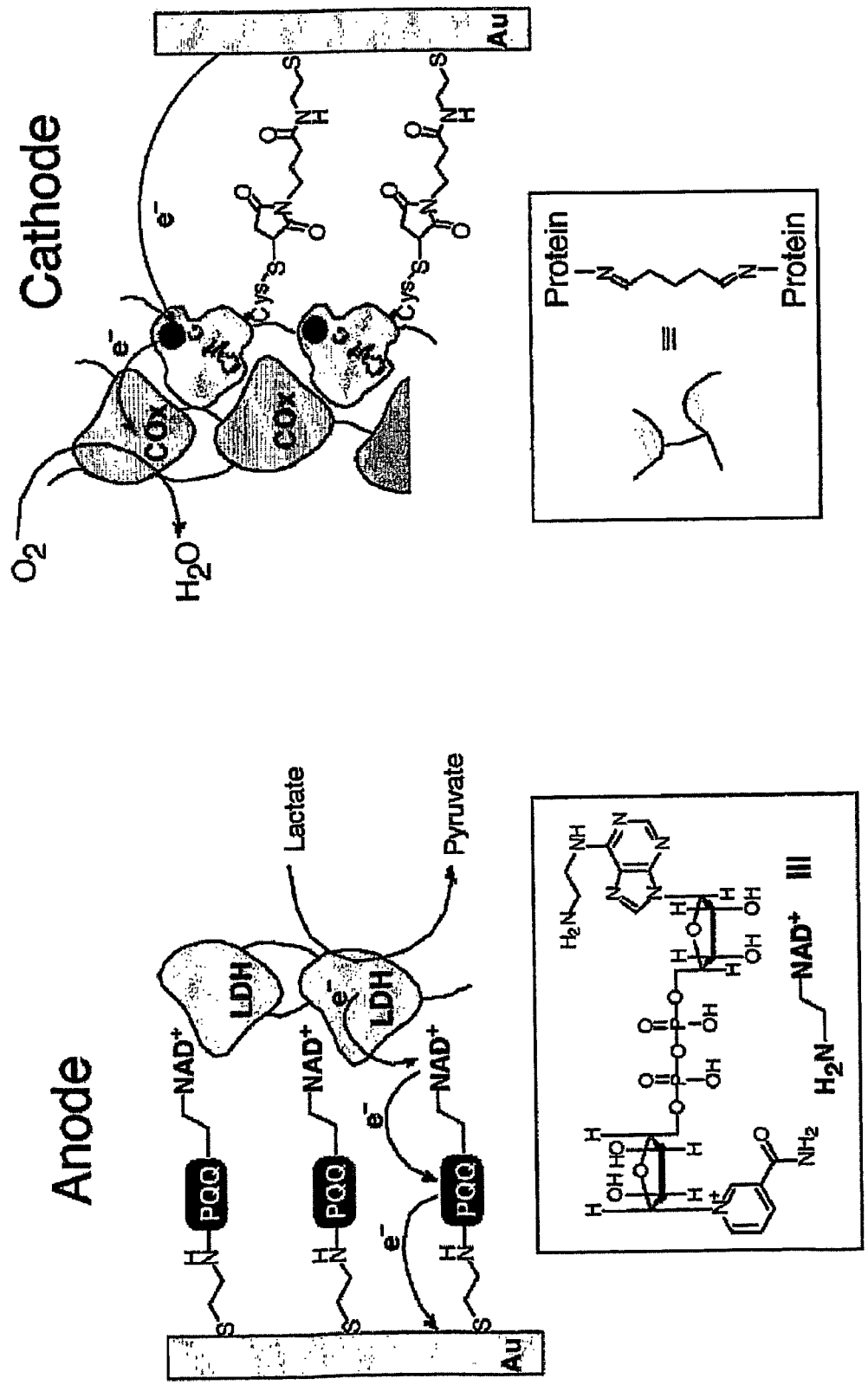
FIG. 6 is a schematic representation of the anode and cathode configurations for a lactate biosensor based on the enzyme Lactate Dehydrogenase (LDH) and Cyt c/COx at the anode and cathode, respectively.

FIG. 6 shows the configuration of a biosensor which measures the concentration of lactate. The anode configuration consists of an integrated lactate dehydrogenase, LDH, layered electrode. To a pyrroloquinolinequinone (PQQ) monolayer linked to an Au-electrode was coupled aminoethyl-functionalyzed NAD (amino-NAD$^+$, compound III in FIG. 6) (3). The affinity-complex formed between LDH and the PQQ-NAD$^+$ monolayer assembly was crosslinked with glutaric dialdehyde to yield the integrated electrically-contacted LDH-functionalized-electrode. The LDH-modified-electrode and the Cyt c/COx layered electrode were employed as the anode and cathode of a self-powered lactate sensing cell, respectively. FIG. 4, curve b shows the open-circuit voltage of the cell, $V_{OC}$ upon the injection of variable concentrations of lactate to the cell under flow conditions. The calibration curve in FIG. 4 (b) indicates that the lactate is sensed in the concentration-range of 1 mM-80 mM. Control experiments reveal that no open-circuit potential is developed in the cell upon injection of ascorbic acid, 50 mM, or glucose, 50 mM, or when lactate, 50 mM, is injected into the cell under an inert atmosphere of argon. These control experiments indicate that the detection of lactate is a result of the simultaneous operation of the anode and cathode as a biofuel cell element. The self-fueled lactate-sensing device is stable for 7 h under continuous operating conditions and the integrated LDH-functionalized-electrode is stable for at least 2 months upon storage in the dry state at 0° C.

Figure 7A:
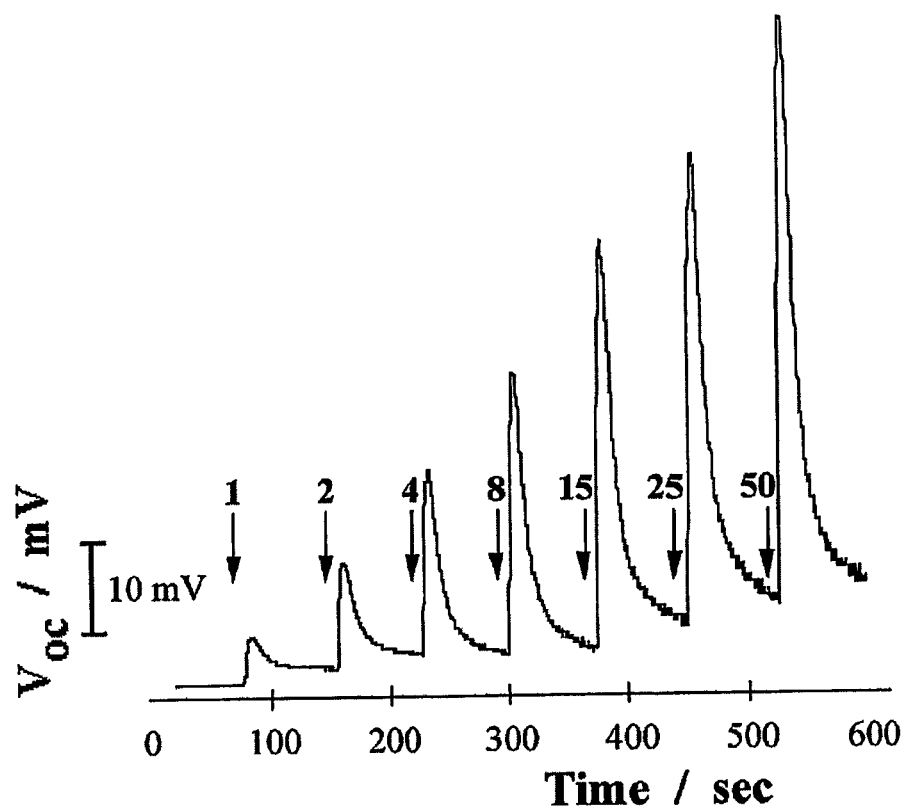
FIG. 7A is a graph showing the open circuit voltage ($V_{OC}$) at variable concentrations of glucose injected into a flow-cell, using the PQQ-FAD/GOx anode.
Figure 7B:
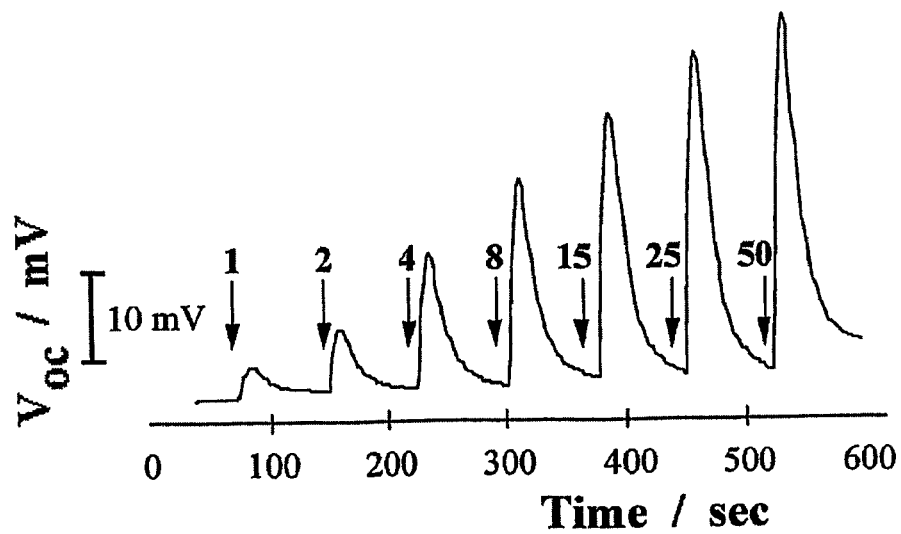
FIG. 7B is a graph showing the open circuit voltage ($V_{OC}$) at variable concentrations of lactate injected into a flow-cell, using the PQQ-NAD$^+$/LDH anode.

FIG. 7 shows the open-circuit voltage ($V_{OC}$) at variable concentration of the substrates into the biofuel cell-based sensor devices: (A) Upon the sensing of glucose using the PQQ-FAD/GOx anode. (B) Upon the sensing of lactate using the PQQ-NAD$^+$/LDH anode. In both systems the Cyt c/COx-functionalized electrode was applied as a cathode. The arrows indicate the injections of samples consisting of 1 mL phosphate buffer, 0.1 M, at pH 7.0, that include the substrate at the concentrations: 1 mM, 2 mM, 4 mM, 8 mM, 15 mM, 25 mM and 50 mM, respectively. All data were recorded in air-saturated 0.1 M phosphate buffer, pH 7.0, 30° C.

In conclusion, the present invention has introduced a novel concept of biosensor systems based on chemical-to-electrochemical energy transformations. While these biofuel cells operate at low efficiency, and have limited applicability as energy suppliers, the extractable electrical power is sufficient to probe the sensing events. In fact, the low electrical power output of the cells has advantages in the sensing processes, since it eliminates redox-transformation of interferrants at the electrode. The sensing devices operate with no external power sources, turning them into attractive invasive sensing elements.

The advantages of the self-powered biosensors of the invention are numerous, inter alia: (i) the sensor consists only of two electrodes and there is no external voltage applied to the electrodes; (ii) as the system is self-powered by biological fluids, the sensor may function as an implanted invasive sensing device; (iii) as no potential is applied on the electrode, the operation of the biosensor device is specific and it is not interfered by contaminants; (iv) since the system does not produce voltage in the absence of the substrate, one concentration of the substrate is enough to calibrate the system.

The invention claimed is:

1. A system for the determination of an analyte in a liquid medium, comprising:
   a self-powered biosensor comprising
      a cathode and an anode;
      redox enzymes on a surface of the cathode and a surface of the anode; and
      a detector for measuring an electrical signal generated by the biosensor while the analyte is being oxidized or reduced,
   the analyte being capable of undergoing a biocatalytic oxidation or reduction in the presence of an oxidizer or reducer, respectively,
   wherein an enzyme carried on one of either the cathode or the anode is capable of catalyzing an oxidation or reduction reaction in which the analyte is oxidized or reduced, respectively,
   wherein another enzyme carried on another of either the cathode or the anode is capable of catalyzing a reaction in which the oxidizer or the reducer are reduced or oxidized, respectively, in the presence of the analyte, and
   wherein the biosensor is configured such that the liquid medium flows from a first end of the biosensor to a second end of the biosensor and between the cathode and the anode.

2. The system of claim 1, wherein the analyte is an organic analyte.

3. The system of claim 2, wherein the organic analyte is selected from the group consisting of sugar molecules, hydroxy, carbonyl or carboxy compounds and amino acids.

4. The system of claim 1, wherein at least one of the cathode or the anode carries an electron mediator group that can transfer electrons between the enzymes and the anode or the cathode substrate.

5. The system of claim 4, wherein both the cathode and the anode carry an electron mediator group on their surface.

6. The system of claim 1, wherein the oxidizer is oxygen that is reduced to water.

7. The system of claim 6, wherein the redox enzymes are cofactor-dependent enzymes and the cofactor is selected from flavin adenine dinucleotide phosphate (FAD), pyrroloquinoline quinone (PQQ), nicotinamide adenine dinucleotide (NAD$^+$), nicotinamide adenine dinucleotide phosphate (NADP$^+$), hemes and iron-sulfur clusters.

8. The system of claim 1, wherein the cathode and the anode are each independently made of or coated by a material selected from gold, platinum, palladium, silver, carbon, copper, and indiumtin oxide.

9. The system of claim 1, wherein the enzymes carried on the anode are selected from glucose oxidase (GOx), lactate dehydrogenase (LDH), fructose dehydrogenase, cholin oxidase, amino oxidase and alcohol dehydrogenase.

10. The system of claim 1, wherein the enzymes carried on the cathode are selected from Lacase and a complex formed of Cytochrome c/Cytochrome oxydase (Cox).

11. The system of claim 1, further comprising a membrane between the anode and the cathode.

12. The system of claim 1, wherein the biosensor is adapted for invasive measurements of an analyte in a body fluid of a tested subject.

13. A method for determining an analyte in a liquid medium, the analyte being capable of undergoing a biocatalytic oxidation or reduction in the presence of an oxidizer or a reducer, respectively, the method comprising:
   (i) providing the system of claim 1;
   (ii) contacting the biosensor of the system with the liquid medium;
   (iii) measuring the electric signal generated between the cathode and the anode, the electric signal being indicative of the presence and/or the concentration of the analyte;
   (iv) determining the analyte based on the signal.

14. The method according to claim 13, wherein the oxidizer is oxygen.

15. The method according to claim 13, comprising adding an oxidizer or a reducer to the medium.

16. The method according to claim 13, wherein the liquid medium is a body fluid, and the method further comprises inserting the biosensor into the body and bringing it into contact with the body fluid and determining the analyte in the body fluid within the body.

17. The method according to claim 16, wherein the body fluid is blood, lymph fluid or cerebro-spinal fluid.

18. The method according to claim 16, wherein the analyte is selected from sugar molecules, lactate, billirubin, alcohols and amino acids.

19. The method according to claim 13, wherein the liquid medium is a body fluid, the method being carried out in a non-invasive manner.

20. The method according to claim 19, wherein the body fluid is blood, lymph fluid or cerebro-spinal fluid.

21. The method according to claim 19, wherein the analyte is selected from sugar molecules, lactate, billirubin, alcohols and amino acids.

22. The system according to claim 1, wherein the anode carries a cofactor-dependent enzyme, wherein said cofactor is nicotinamide adenine dinucleotide (NAD+).

23. The system according to claim 22, wherein the anode carries a PQQ-NAD+assembly.

* * * * *